United States Patent [19]
Golan

[11] Patent Number: 5,729,479
[45] Date of Patent: Mar. 17, 1998

[54] MULTIFUNCTIONAL DIET CALCULATOR

[75] Inventor: Yafa Golan, Tel Aviv, Israel

[73] Assignee: Diet-Deal Ltd., Tel Aviv, Israel

[21] Appl. No.: 571,120

[22] Filed: Dec. 12, 1995

[30] Foreign Application Priority Data

Sep. 14, 1995 [IL] Israel ............................ 115316

[51] Int. Cl.$^6$ ...................... G06F 15/00; G06F 15/42
[52] U.S. Cl. ............................ 364/709.02; 128/630
[58] Field of Search ............... 364/706, 709.01, 364/709.02, 709.03, 709.14, 709.15; 128/630

[56] References Cited

U.S. PATENT DOCUMENTS

| | | | |
|---|---|---|---|
| 4,221,959 | 9/1980 | Seller | 377/13 |
| 4,224,020 | 9/1980 | Neyret | 313/44 |
| 4,244,020 | 1/1981 | Ratcliff | 364/413.29 |
| 4,321,674 | 3/1982 | Krames et al. | 364/413.29 |
| 4,380,802 | 4/1983 | Segar et al. | 128/630 |
| 4,636,624 | 1/1987 | Ishida et al. | 250/201.8 |
| 4,686,624 | 8/1987 | Blum et al. | 364/413.29 |
| 4,796,182 | 1/1989 | Dubroff | 364/413.29 |
| 4,855,945 | 8/1989 | Sakai | 364/709.02 |
| 4,864,592 | 9/1989 | Lee | 377/5 |
| 4,891,756 | 1/1990 | Williams, III | 364/413.29 |
| 4,911,256 | 3/1990 | Attikiouzel | 364/709.13 X |
| 4,924,389 | 5/1990 | Gerbaulet et al. | 364/413.29 |
| 4,924,398 | 5/1990 | Fujiwara | 364/431.11 |
| 4,965,553 | 10/1990 | Delbiondo, II et al. | 340/573 |
| 5,019,974 | 5/1991 | Becker | 364/709.02 |
| 5,233,520 | 8/1993 | Kretsch et al. | 364/413.29 |
| 5,388,043 | 2/1995 | Hettinger | 364/461 |

*Primary Examiner*—Chuong Dinh Ngo
*Attorney, Agent, or Firm*—Browdy and Neimark

[57] ABSTRACT

This invention discloses a multifunctional diet calculator comprising a user operable input for receiving at least one target amount of at least one food substance to be consumed by a user and information regarding actual consumption of food substances by the user, a memory for storing target amounts of the at least one food substance and cumulative actual consumption thereof over a given period, a computation unit for determining the relationship between the target amounts and the cumulative actual consumption, an output device showing the relationship between the target amounts and the cumulative actual consumption, a prompt unit for providing at least one user sensible prompt during the given period for reminding the user to consume a food substance and a clock for providing timing information for at least the computation unit and the prompt unit.

12 Claims, 6 Drawing Sheets

MULTIFUNCTIONAL DIET CALCULATOR

FIELD OF THE INVENTION

The present invention relates to calculators generally and more particularly to diet calculators.

BACKGROUND OF THE INVENTION

Various types of calculators are known for determining and keeping track of food intake and the intake of food constituents. The following U.S. Patents are believed to represent the state of the art: U.S. Pat. Nos. 4,221,959; 4,224,020; 4,686,624; 4,796,182; 4,855,945; 4,864,592; 4,924,398; 4,965,553; and 5,233,520. U.S. Pat. No. 4,855,945 is believed to be the most relevant and shows a portable calculator which compares necessary amounts of food constituents with actual amounts taken in during each day.

SUMMARY OF THE INVENTION

The present invention seeks to provide a multifunctional diet calculator which is operative to provide prompts to a user in addition to keeping track of food intake. The prompts may be useful in ensuring that the user consumes desired amounts of substances, such as water or pills, which are helpful in ensuring success of a diet or other regime.

There is thus provided, in accordance with a preferred embodiment of the present invention, a multifunctional diet calculator including a user operable input for receiving at least one target amount of at least one food substance to be consumed by a user and information regarding actual consumption of food substances by the user, a memory for storing target amounts of the at least one food substance and cumulative actual consumption thereof over a given period, a computation unit for determining the relationship between the target amounts and the cumulative actual consumption, an output device showing the relationship between the target amounts and the cumulative actual consumption, a prompt unit for providing at least one user sensible prompt during the given period for reminding the user to consume a food substance, and a clock for providing timing information for at least the computation unit and the prompt unit.

Further in accordance with a preferred embodiment of the present invention, at least one food substance may include calories and/or cholesterol.

There is also provided, in accordance with a preferred embodiment of the present invention, a substance intake calculator including a user operable input for receiving at least one target amount of at least one food substance to be consumed by a user and information regarding actual consumption of solid and liquid food substances by the user, a memory for storing target amounts of the at least one food substance and a target liquid volume and cumulative actual consumption of the at least one food substance and of liquid over a given period, a computation unit for determining the relationship between the target amounts and the cumulative actual consumption, and an output device showing the relationship between the target amounts and the cumulative actual consumption.

Still further in accordance with a preferred embodiment of the present invention, the information regarding actual consumption of liquid food substances includes, for each instance of liquid food substance consumption, a single indication of consumption of liquid food substance.

Further in accordance with a preferred embodiment of the present invention, the calculator also includes a prompt unit for providing at least one user sensible prompt during the given period for reminding the user to consume a food substance, and a clock for providing timing information for at least the computation unit and the prompt unit.

Also provided, in accordance with a preferred embodiment of the present invention, is a multifunctional diet calculator including a user operable input for receiving at least one target amount of at least one food substance to be consumed by a user and information regarding actual consumption of food substances by the user, a memory for storing target amounts of the at least one food substance for a given period and cumulative actual consumption thereof over the given period, a computation unit for determining the relationship between the target amounts and the cumulative actual consumption, an output device showing the relationship between the target amounts and the cumulative actual consumption, a prompt unit, responsive to the computation unit, for providing at least one user sensible prompt once the given period has elapsed for reminding the user to consume a food substance if actual consumption is less than the target amounts, and a clock for providing timing information for the prompt unit.

Also provided, in accordance with a preferred embodiment of the present invention, is a multifunctional diet calculation method including receiving from a user at least one target amount of at least one food substance to be consumed by a user and information regarding actual consumption of food substances by the user, storing target amounts of the at least one food substance and cumulative actual consumption thereof over a given period, determining the relationship between the target amounts and the cumulative actual consumption, outputting the relationship between the target amounts and the cumulative actual consumption, providing at least one user sensible prompt during the given period for reminding the user to consume a food substance, and for providing timing information for at least the computation unit and the prompt unit.

Further in accordance with a preferred embodiment of the present invention, the at least one food substance may be calories and/or cholesterol.

Also provided, in accordance with a preferred embodiment of the present invention, is a substance intake calculation method including receiving from a user at least one target amount of at least one food substance to be consumed by a user and information regarding actual consumption of solid and liquid food substances by the user, storing target amounts of the at least one food substance and a target liquid volume and cumulative actual consumption of the at least one food substance and of liquid over a given period, determining the relationship between the target amounts and the cumulative actual consumption, and outputting the relationship between the target amounts and the cumulative actual consumption.

Further in accordance with a preferred embodiment of the present invention, the information regarding actual consumption of liquid food substances includes, for each instance of liquid food substance consumption, a single indication of consumption of liquid food substance.

Still further in accordance with a preferred embodiment of the present invention, the method includes providing at least one user sensible prompt during the given period for reminding the user to consume a food substance, and providing timing information for at least the computation unit and the prompt unit.

Further provided, in accordance with a preferred embodiment of the present invention, is a multifunctional diet calculation method including receiving from a user at least one target amount of at least one food substance to be consumed by a user and information regarding actual consumption of food substances by the user, storing target amounts of the at least one food substance for a given period and cumulative actual consumption thereof over the given period, determining the relationship between the target amounts and the cumulative actual consumption, outputting the relationship between the target amounts and the cumulative actual consumption, providing, responsive to the relationship, at least one user sensible prompt once the given period has elapsed for reminding the user to consume a food substance if actual consumption is less than the target amounts, and providing timing information for the prompt providing step.

BRIEF DESCRIPTION OF THE DRAWINGS

The present invention will be understood and appreciated from the following detailed description, taken in conjunction with the drawings in which.

DETAILED DESCRIPTION OF PREFERRED EMBODIMENTS

Figure 1:
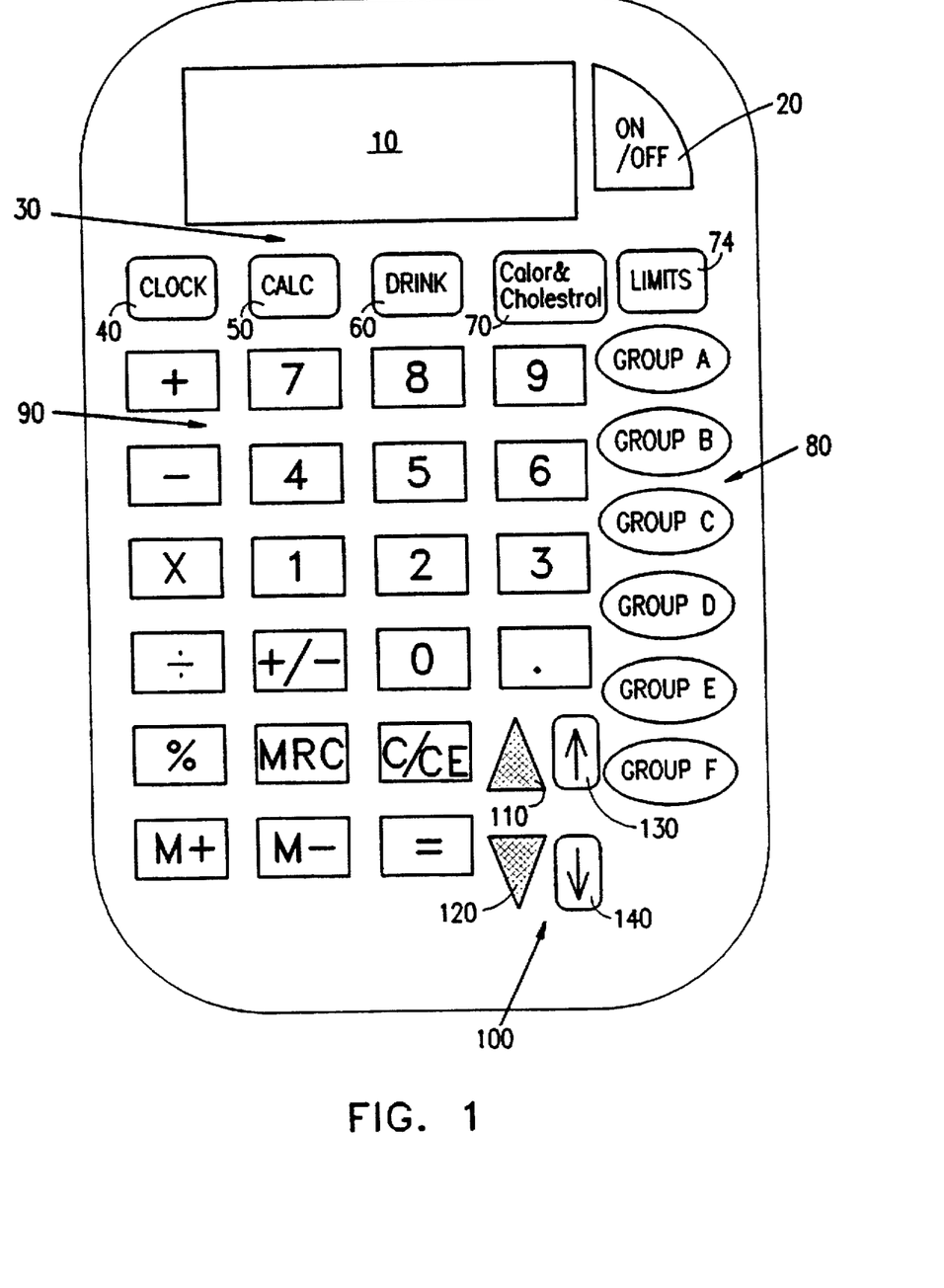
FIG. 1 is a simplified pictorial illustration of a multifunctional substance intake calculator constructed and operative in accordance with a preferred embodiment of the present invention.

Reference is now made to FIG. 1 which is a simplified pictorial illustration of a multifunctional substance intake calculator constructed and operative in accordance with a preferred embodiment of the present invention.

The calculator of FIG. 1 includes a display 10 and the following user operable inputs:

an on/off button 20;

an array 30 of mode selection buttons such as a clock mode selection button 40, a calculator mode selection button 50, an optional drink (liquid food) mode selection button 60, a food substance mode selection button 70, and a limits mode selection button 74.

an array 80 of food substance group buttons;

an array 90 of conventional calculator operating buttons; and an array 100 of food substance browsing buttons allowing a user to browse among the food substances within a particular food substance group. Preferably the array 100 includes a "page up" button 110, a "page down" button 120, a "forward" button 130 for advancing from one food substance to the next and a "backward" button 140 for advancing from a food substance back to a preceding food substance within the same group.

The apparatus of FIG. 1 typically has a plurality of modes of operation such as a "clock mode", in which alarms are set, a "calculator mode" in which calculations may be made, an optional "drink mode" in which information regarding liquid consumed may be entered, a "limits mode", also termed herein "calories mode", in which limits on food components allowed per day (e.g. calories) are set and a "food substance mode", also termed herein "group mode", in which information regarding foods consumed may be entered. If the drink mode is omitted, information regarding liquid foods consumed is preferably accumulated by the system so as to store an indication of the total volume of liquid consumed.

The calculator operating buttons may also be employed within modes of operation other than the calculator mode. For example, the "+" button may be employed in the clock mode to activate a user-defined alarm identified by a cursor, in the drink mode to indicate that an amount of liquid has been drunk, in the limit mode to increment the maximum number of calories allowed per day and in the food substance mode to indicate that a food identified by a cursor has been consumed. The "−" button may be employed in the clock mode to deactivate a user-defined alarm identified by a cursor, in the drink mode to cancel a previous indication that an amount of liquid has been drunk, in the limit mode to decrement the maximum number of calories allowed per day and in the food substance mode to cancel a previous indication that a food identified by a cursor has been consumed.

The multiplication and digit buttons may be employed in the drink mode to indicate that a fraction of a cup of liquid has been consumed. For example, the sequence "×2.5+" would indicate that 2.5 cups of liquid have been consumed. Similarly, the multiplication and digit buttons may be employed in the food mode to indicate that a quantity, other than a system-defined quantity, of a food identified by the cursor has been consumed. For example, if the cursor indicates the following food substance entry: "Bread—70 calories—one slice", the sequence "×3+" would indicate that 3 slices of bread have been consumed.

FIGS. 2A–2D are simplified pictorial illustrations of four typical screen displays which may appear on the screen of FIG. 1.

Figure 2A:
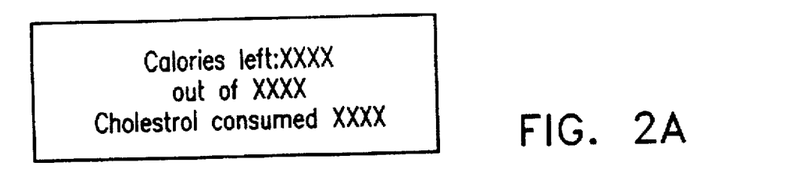
FIGS. 2A–2D are simplified pictorial illustrations of four screen displays which may appear on the screen of FIG. 1.

The screen of FIG. 2A appears when the food substance mode is selected.

Figure 2B:
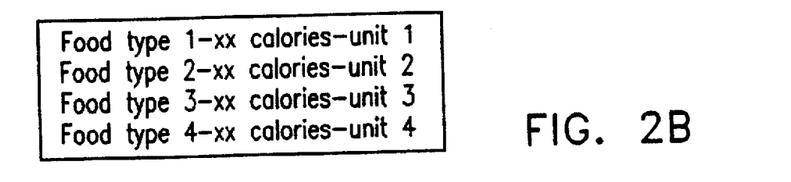

The screen of FIG. 2B appears when a food substance group has been selected using one of the buttons in array 80. Each line preferably includes a food name, a unit of the food, and the amount of at least one food component within that unit of that food. A typical line might be: "Bread—70 calories—one slice".

Figure 2C:
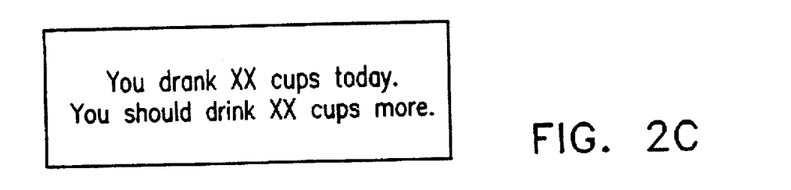

The screen of FIG. 2C appears when the drink mode is selected. Optionally, the drink mode may be omitted and the information appearing on the screen display of FIG. 2C may be added to the information appearing on the screen display of FIG. 2A.

Figure 2D:
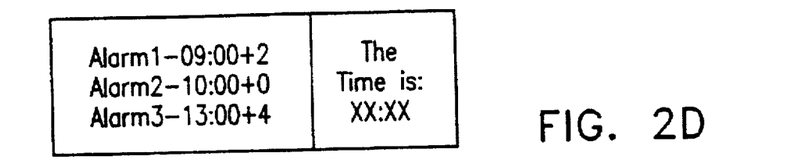

The screen of FIG. 2D appears when the clock mode is selected. The following information is displayed for each of a plurality of alarms, such as three alarms in the illustrated embodiment:

The time at which the alarm is to ring and, optionally, the alarm inducing criterion. The alarm inducing criterion typically comprises an amount of a food component or an amount of liquid which is to be consumed by the time at which the alarm is to ring. In the illustrated example, the first alarm is to ring at 9:00 if the user has consumed less than 2 cups of liquid, the second alarm is to ring at 10:00 regardless of liquid consumed (because, perhaps, the user wants to be reminded to take pills at that time), and the third alarm is to ring at 13:00 if the user has consumed less than 4 cups of liquid by that time.

Figure 3:
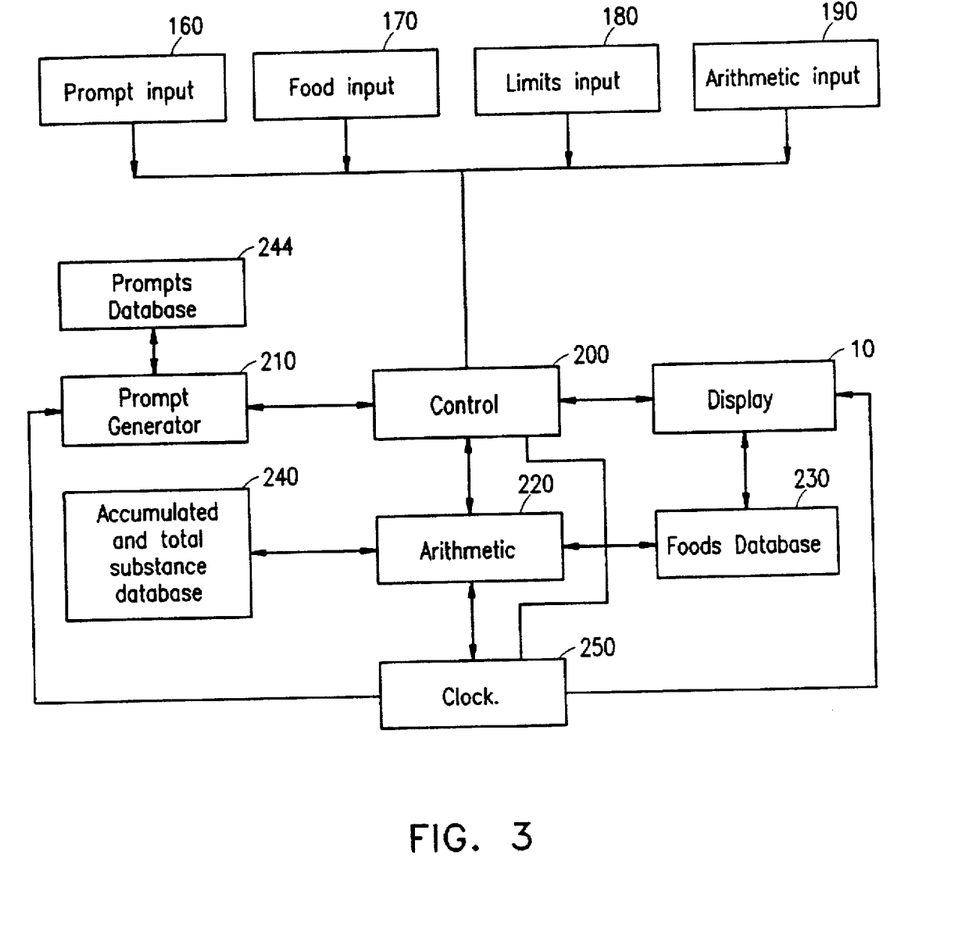
FIG. 3 is a simplified block diagram of the substance intake calculator of FIG. 1.

FIG. 3 is a simplified block diagram of the substance intake calculator of FIG. 1. As shown, the system can accept a plurality of types of input which typically include:

a. prompt input 160 defining alarms, b. food/drink input 170 defining amount of drink and types of food consumed, c. limits input 180 defining limits, or the maximum amounts of substances, such as calories and/or cholesterol, that an individual user is to consume over any given period of time, for example daily, and d. Arithmetic input 190 defining arithmetic operations to be performed.

The input is received by a control unit 200 which is operatively associated with a prompt generator 210 such as an audio alarm, display 10 (FIG. 1), an arithmetic unit 220, a foods database 230, an accumulated and total substance database 240, a prompts database 244 and a clock 250.

The prompt generator 210 provides a prompt such as an audio alarm at appropriate times as stored in the prompts database 244, as timed by the clock 250. Optionally, as described in more detail below with reference to FIG. 5, prompts are only provided if, at a user-defined time, a certain criterion has been met.

The arithmetic unit 220 is preferably operative to perform simple arithmetic computations keyed in by a user, and also preferably:

a. to accumulate amounts of substances, such as calories and/or cholesterol, in foods keyed in by a user b. to accumulate volumes of liquid consumed by a user; and c. to determine whether user-defined prompt criteria have been met at predetermined times.

The foods database typically comprises, for each food, the food's name, the group or groups to which the food belongs, an indication of a unit of consumption of that food, the substances (calories and/or cholesterol, for example) present in that unit of that food, and an indication of whether or not the food is a liquid.

According to a preferred embodiment of the present invention, the foods are not partitioned into groups but rather are divided into groups such that some foods may appear within more than one group, thereby to facilitate finding of a particular food. One example of groups may be: meats, dairy, grains, fast foods, fruits and vegetables and desserts.

It is appreciated that the apparatus of FIG. 3 provides a synergistic, interacting combination of elements which is not present in prior art substance consumption systems. As described herein, the apparatus of FIG. 3 preferably accumulates, for liquid foods, both food substance information, similarly to the operation of the apparatus for non-liquid foods, and volume information. It is preferably not necessary for the user to separately record consumption of a liquid food in both a drink recording mode and in a food component recording mode.

As described herein, the apparatus of FIG. 3 preferably not only accumulates and displays information regarding food consumed, it also provides prompts regarding inappropriate consumption of foods at user-defined points in time. Preferably, simple prompts are also provided at user-defined points, independent of any criteria. The simple prompts are useful, for example, to remind users to take medication.

Figure 4A:
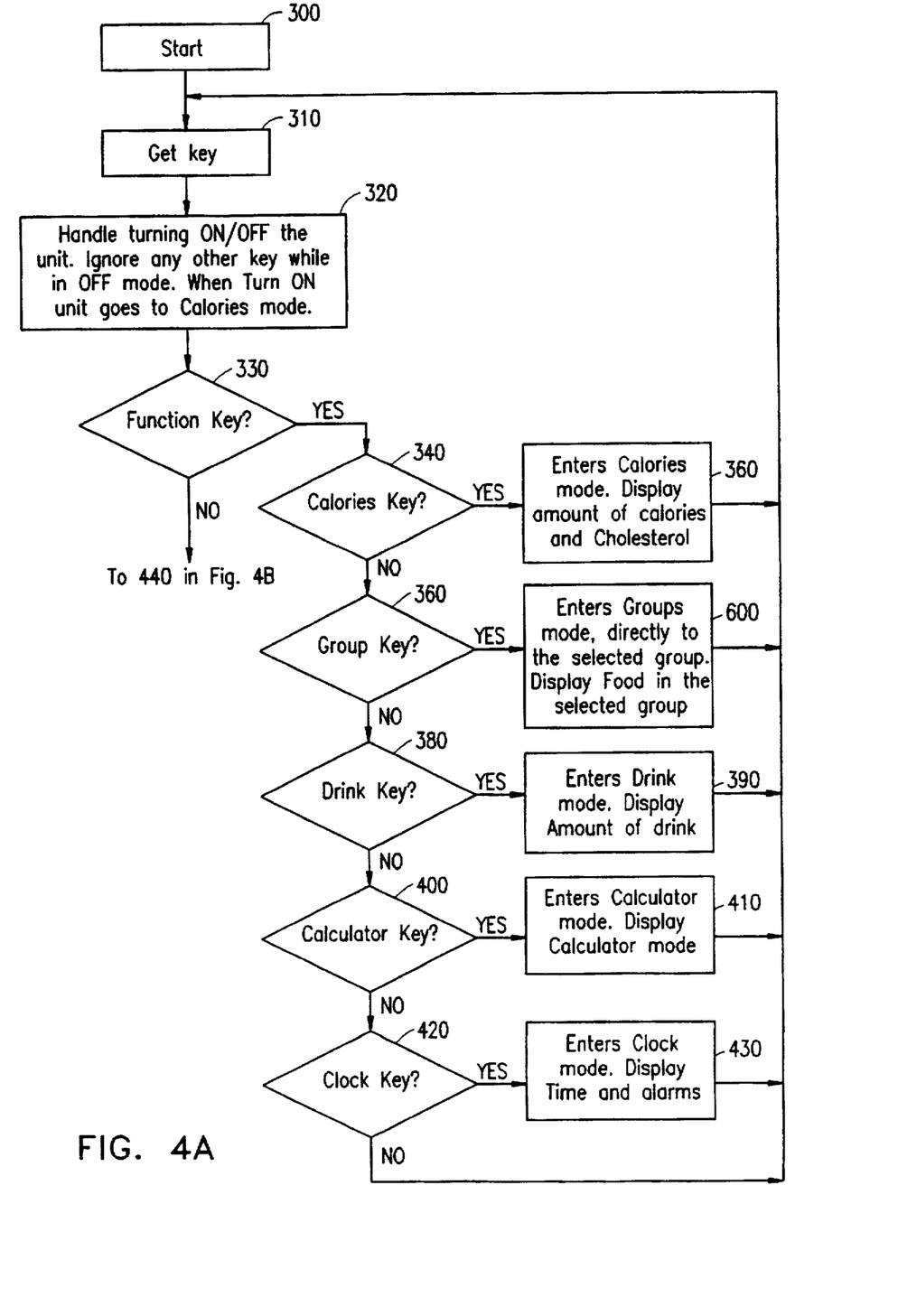
FIGS. 4A and 4B, taken together, are a simplified flowchart illustration of a preferred method of operation of the substance intake calculator of FIGS. 1–3.
Figure 4B:
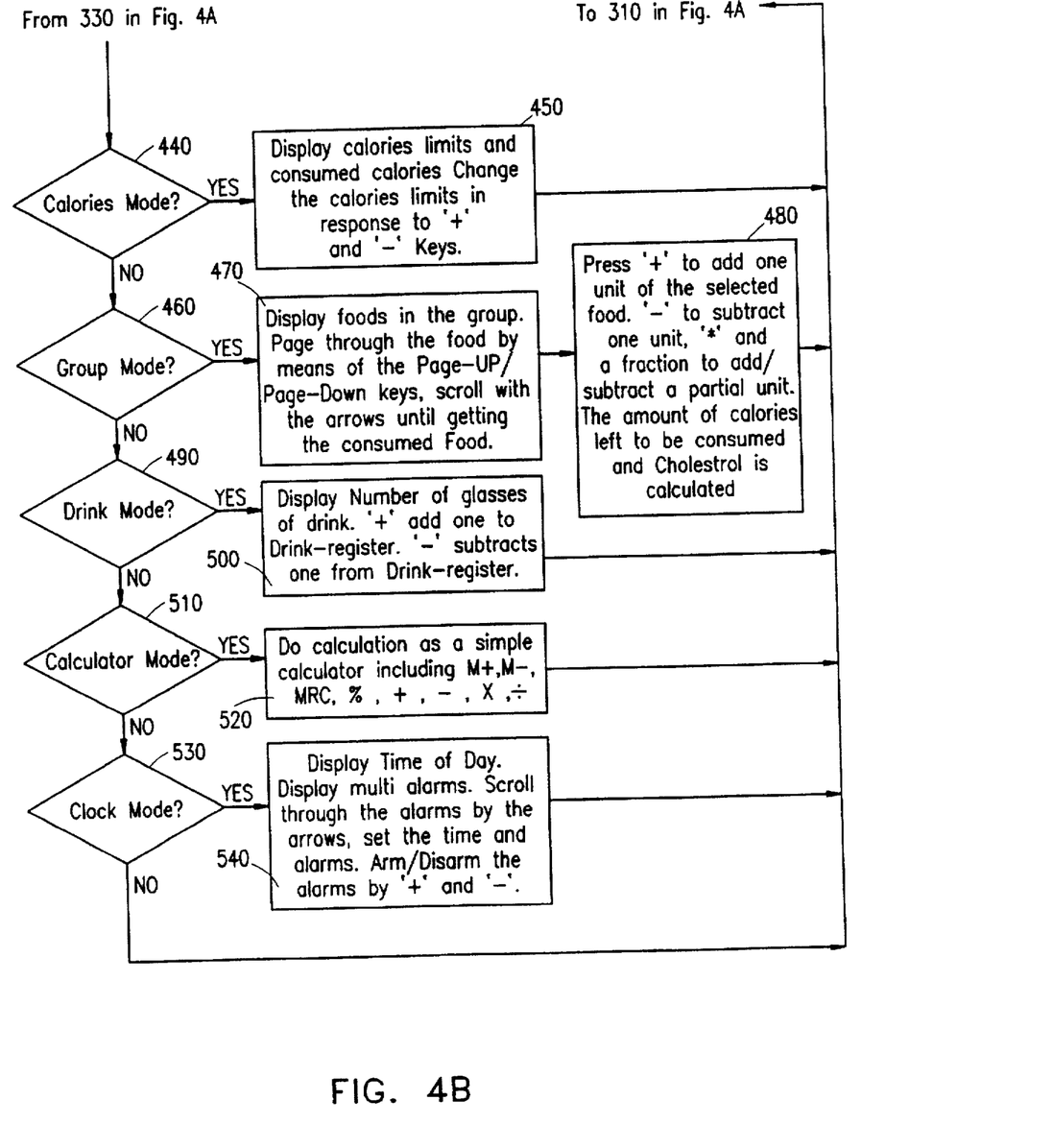

Reference is now made to FIGS. 4A and 4B, taken together, which are a simplified flowchart illustration of a preferred mode of operation of the substance intake calculator of FIGS. 1-3. In FIGS. 4A and 4B, the term "function key" refers to the mode selection buttons 30 and the "group mode key" refers to the food substance group buttons 80.

Figure 5:
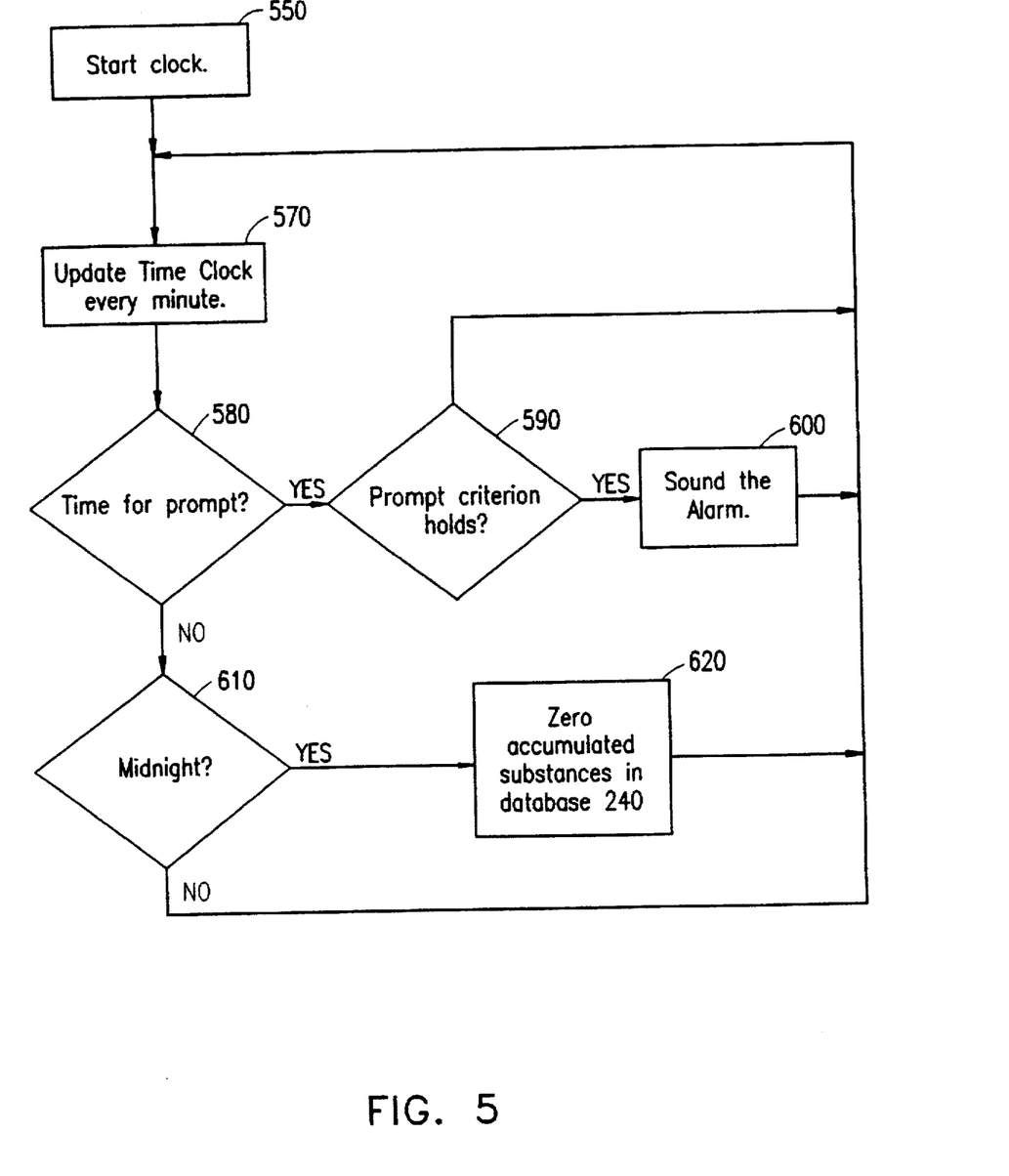
FIG. 5 is a simplified flowchart illustration of a preferred method of operation for the prompt unit of FIG. 3.

FIG. 5 is a simplified flowchart illustration of a preferred mode of operation for the prompt generator of FIG. 3.

It is appreciated that the software components of the present invention may, if desired, be implemented in ROM (read-only memory) form. The software components may, generally, be implemented in hardware, if desired, using conventional techniques.

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will be appreciated by persons skilled in the art that the present invention is not limited to what has been particularly shown and described hereinabove. Rather, the scope of the present invention is defined only by the claims that follow:

I claim:

1. A multifunctional diet calculator comprising:

a user operable input for receiving at least one target amount of at least one food substance to be consumed by a user and information regarding actual consumption of food substances by the user;

a memory for storing target amounts of the at least one food substance and cumulative actual consumption thereof over a given period;

a computation unit for determining the relationship between the target amounts and the cumulative actual consumption;

an output device showing the relationship between the target amounts and the cumulative actual consumption;

a prompt unit responsive to the relationship between the target amounts and the cumulative actual consumption for providing at least one user sensible prompt during the given period for reminding the user to consume a food substance; and a clock for providing timing information for at least the computation unit and the prompt unit.

2. A calculator according to claim 1 wherein the at least one food substance may be one or more of the following group:

calories;

water; and cholesterol.

3. A substance intake calculator comprising:

a user operable input for receiving at least one target amount of at least one food substance to be consumed by a user and information regarding actual consumption of solid and liquid food substances by the user;

a memory for storing target amounts of the at least one food substance and a target liquid volume and cumulative actual consumption of the at least one food substance and of liquid over a given period;

a computation unit for determining the relationship between the target amounts and the cumulative actual consumption; and an audio output device responsive to the relationship between the target amounts and the cumulative actual consumption.

4. A calculator according to claim 3 wherein said information regarding actual consumption of liquid food substances includes, for each instance of liquid food substance consumption, a single indication of consumption of liquid food substance.

5. A calculator according to claim 3 and wherein said audio output device includes:
- a prompt unit for providing at least one user sensible prompt during the given period for reminding the user to consume a food substance; and wherein said calculator also comprises:
- a clock for providing timing information for at least the computation unit and the prompt unit.

6. A multifunctional diet calculator comprising:
- a user operable input for receiving at least one target amount of at least one food substance to be consumed by a user and information regarding actual consumption of food substances by the user;
- a memory for storing target amounts of the at least one food substance for a given period and cumulative actual consumption thereof over the given period;
- a computation unit for determining the relationship between the target amounts and the cumulative actual consumption;
- an output device showing the relationship between the target amounts and the cumulative actual consumption;
- a prompt unit, responsive to the computation unit, for providing at least one user sensible prompt once the given period has elapsed for reminding the user to consume a food substance if actual consumption is less than said target amounts; and
- a clock for providing timing information for the prompt unit.

7. A multifunctional diet calculation method comprising:
- receiving from a user at least one target amount of at least one food substance to be consumed by a user and information regarding actual consumption of food substances by the user;
- storing target amounts of the at least one food substance and cumulative actual consumption thereof over a given period;
- determining the relationship between the target amounts and the cumulative actual consumption;
- outputting the relationship between the target amounts and the cumulative actual consumption; and
- providing at least one user sensible prompt during the given period responsive to the relationship between the target amounts and the cumulative actual consumption for reminding the user to consume a food substance.

8. A method according to claim 7 wherein the at least one food substance may be one or more of the following group:

calories;
water; and
cholesterol.

9. A substance intake calculation method comprising:
- receiving from a user at least one target amount of at least one food substance to be consumed by a user and information regarding actual consumption of solid and liquid food substances by the user;
- storing target amounts of the at least one food substance and a target liquid volume and cumulative actual consumption of the at least one food substance and of liquid over a given period;
- determining the relationship between the target amounts and the cumulative actual consumption; and
- outputting an audio indication responsive to the relationship between the target amounts and the cumulative actual consumption.

10. A method according to claim 9 wherein said information regarding actual consumption of liquid food substances includes, for each instance of liquid food substance consumption, a single indication of consumption of liquid food substance.

11. A method according to claim 9 and wherein outputting an audio indication comprises:
- providing at least one user sensible prompt during the given period for reminding the user to consume a food substance.

12. A multifunctional diet calculation method comprising:
- receiving from a user at least one target amount of at least one food substance to be consumed by a user and information regarding actual consumption of food substances by the user;
- storing target amounts of the at least one food substance for a given period and cumulative actual consumption thereof over the given period;
- determining the relationship between the target amounts and the cumulative actual consumption;
- outputting the relationship between the target amounts and the cumulative actual consumption;
- providing, responsive to said relationship, at least one user sensible prompt once the given period has elapsed for reminding the user to consume a food substance if actual consumption is less than said target amounts; and
- providing timing information for the prompt providing step.

* * * * *